United States Patent
Owens et al.

(10) Patent No.: US 7,094,936 B1
(45) Date of Patent: Aug. 22, 2006

(54) PROCESS FOR PREPARING HALOGENATED ALKANES

(75) Inventors: Stephen Owens, White Pine, TN (US); Andrew Jackson, El Dorado, AR (US); Vimal Sharma, El Dorado, AR (US); Mitchel Cohn, West Lafayette, IN (US); John Cheng-Ping Qian, West Lafayette, IN (US); Julia Ann Sacarias, El Dorado, AR (US); Yuichi Iikubo, West Lafayette, IN (US)

(73) Assignee: Great Lakes Chemical Corporation, West Lafayette, IN (US)

( * ) Notice: Subject to any disclaimer, the term of this patent is extended or adjusted under 35 U.S.C. 154(b) by 0 days.

(21) Appl. No.: 10/688,230

(22) Filed: Oct. 16, 2003

Related U.S. Application Data

(63) Continuation of application No. 10/133,551, filed on Apr. 26, 2002, which is a continuation of application No. 09/909,695, filed on Jul. 20, 2001, now abandoned.

(51) Int. Cl.
C07C 17/278 (2006.01)
C07C 17/272 (2006.01)
C07C 17/26 (2006.01)

(52) U.S. Cl. .............. 570/257; 570/261; 570/246; 570/247; 570/170; 570/171; 570/172; 570/175

(58) Field of Classification Search ............... 570/257, 570/261, 246, 247, 170, 171, 172, 175
See application file for complete search history.

(56) References Cited

U.S. PATENT DOCUMENTS

| | | | |
|---|---|---|---|
| 2,467,123 A | 4/1949 | Fleck et al. | |
| 2,593,451 A | 4/1952 | Hill et al. | |
| 4,535,194 A | 8/1985 | Woodard | |
| 4,816,609 A | 3/1989 | Harley | |
| 5,171,901 A | 12/1992 | Gassen et al. | |
| 5,395,997 A | 3/1995 | Van Der Puy et al. | |
| 5,414,165 A | 5/1995 | Nappa et al. | |
| 5,545,774 A | 8/1996 | Rao | |
| 5,616,819 A | 4/1997 | Boyce et al. | |
| 5,633,413 A | 5/1997 | Van Der Puy et al. | |
| 5,763,706 A | 6/1998 | Tung et al. | |
| 5,792,893 A | 8/1998 | Wilson et al. | ............ 570/257 |
| 5,811,604 A | 9/1998 | Benson et al. | |
| 5,856,595 A | 1/1999 | Merkel et al. | |
| 5,895,825 A | 4/1999 | Elsheikh et al. | |
| 5,902,911 A | 5/1999 | Rao et al. | |
| 5,902,914 A | 5/1999 | Rygas et al. | |
| 6,013,846 A | 1/2000 | Wismer et al. | |
| 6,018,084 A | 1/2000 | Nakada et al. | |
| 6,066,769 A | 5/2000 | Nappa et al. | |
| 6,187,978 B1 | 2/2001 | Rygas et al. | |
| 6,211,135 B1 | 4/2001 | Miller et al. | |
| 6,274,779 B1 | 8/2001 | Merkel et al. | |
| 6,291,729 B1 | 9/2001 | Rao | |
| 6,291,730 B1 | 9/2001 | Baker et al. | |
| 6,313,360 B1 | 11/2001 | Wilson et al. | |
| 6,316,682 B1 * | 11/2001 | Nakada et al. | ............ 570/170 |
| 6,329,559 B1 | 12/2001 | Sievern et al. | |
| 6,376,727 B1 | 4/2002 | Rao et al. | |
| 6,388,147 B1 | 5/2002 | Rao et al. | |
| 6,472,574 B1 | 10/2002 | Rao et al. | |
| 6,534,688 B1 | 3/2003 | Klausmeyer | ............ 570/264 |
| 6,548,720 B1 | 4/2003 | Manogue et al. | |
| 2003/0028057 A1 | 2/2003 | Owens et al. | ............ 570/257 |
| 2004/0225166 A1 | 11/2004 | Wilson et al. | ............ 570/171 |

FOREIGN PATENT DOCUMENTS

| | | |
|---|---|---|
| CA | 2.073.533 | 7/1992 |
| EP | 0 061 174 A1 | 9/1982 |
| EP | 0 131 561 A1 | 4/1984 |
| JP | 49-66613 A | 6/1974 |
| WO | WO 95/04022 | 2/1995 |
| WO | WO03/080549 A1 | 10/2003 |

OTHER PUBLICATIONS

Burton et al. Copper Chloride-Ethanolamine Catalyzed Addition of Polyhaloalkanes to 1-Octene J. Organic Chemistry 35(5) 1339:1342 May 1970.

Brunet, S., et al., "Catalytic liquid phase fluorinations with Sb-Ti mixed halides", Journal of Molecular Catalysis A: Chemical, 108 (1996) pp. 11-14.

* cited by examiner

Primary Examiner—Elvis O. Price
(74) Attorney, Agent, or Firm—Wells St. John P.S.

(57) ABSTRACT

Methods and materials are provided for the production and purification of halogenated compounds and intermediates in the production of 1,1,1,3,3-pentafluoropropane. In a preferred embodiment, the process steps include: (1) reacting carbon tetrachloride with vinyl chloride to produce 1,1,1,3,3-pentachloropropane; (2) dehydrochlorinating the 1,1,1,3,3-pentachloropropane with a Lewis acid catalyst to produce 1,1,3,3-tetrachloropropene; (3) fluorinating the 1,1,3,3-tetrachloropropene to produce 1-chloro-3,3,3-trifluoropropene; (4) fluorinating the 1-chloro-3,3,3-trifluoropropene to produce a product mixture containing 1,1,1,3,3-pentafluoropropane; and (5) separating 1,1,1,3,3-pentafluoropropane from by-products.

13 Claims, No Drawings

PROCESS FOR PREPARING HALOGENATED ALKANES

CROSS REFERENCE TO RELATED APPLICATION

This application is a continuation of U.S. application Ser. No. 10/133,551 filed on Apr. 26, 2002, which is a continuation of U.S. patent application Ser. No. 09/909,695 filed Jul. 20, 2001 now abandoned.

FIELD OF THE INVENTION

The present invention relates to methods and apparatus for the preparation and purification of halogenated hydrocarbons. More particularly, the present invention relates to the production and purification of 1,1,1,3,3-pentafluoropropane ($CF_3CH_2CF_2H$, HFC-245fa).

BACKGROUND OF THE INVENTION

Numerous methods are disclosed for the preparation of 1,1,1,3,3-pentafluoropropane ($CF_3CH_2CF_2H$, HFC-245fa). These methods vary widely, due in part to the different starting materials and reaction conditions involved.

HFC-245fa is a known chemical species that has found use as a foam blowing agent and also as a refrigerant. HFC-245fa has been prepared according to one known process via the treatment of 1-chloro-3,3,3-trifluoropropene ($CHCl=CHCF_3$, HCFC-1233zd) with excess HF. However, purification of HFC-245fa from the resulting reaction mixture is difficult because HFC-245fa, HCFC-1233zd and HF are difficult to separate by distillation.

U.S. Pat. No. 6,018,084 to Nakada et al., discloses a process wherein 1,1,1,3,3-pentachloropropane ($CCl_3CH_2CHCl_2$) is reacted with HF in the gaseous phase in the presence of a fluorination catalyst to form HCFC-1233zd, which is then reacted with HF in the gaseous phase to produce (HFC-245fa).

U.S. Pat. No. 5,895,825 to Elsheikh et al., discloses a process wherein HCFC-1233zd is reacted with HF to form 1,3,3,3-tetrafluoropropene ($CF_3CH=CHF$) followed by further HF addition to form HFC-245fa.

Although the above described methods serve to produce HFC-245fa, these preparations are characterized by numerous disadvantages, including expensive raw materials, poor yields and poor selectivity which preclude their use on a commercial scale.

SUMMARY OF THE INVENTION

In brief, the present invention provides novel methods and materials for the preparation of halogenated hydrocarbons from readily available starting materials, particularly carbon tetrachloride and vinyl chloride. The present invention discloses new and improved processes for preparing precursors and intermediates, in the production of HFC-245fa. The processes are characterized by high selectivity, conversion and yield, and offer significant economic advantages over prior art preparations.

One aspect of the present invention is to provide a method for the production of HFC-245fa from readily available starting materials, particularly carbon tetrachloride and vinyl chloride. In one embodiment of the present invention, 1,1,1,3,3-pentachloropropane is produced by supplying a reactor with a combination of carbon tetrachloride, vinyl chloride and a metal chelating agent.

The 1,1,1,3,3-pentachloropropane is then dehydrochlorinated with a Lewis acid catalyst to produce 1,1,3,3-tetrachloropropene, which is then hydro fluorinated in multiple steps to produce HFC-245fa.

A further aspect of this invention is to provide a method which has high conversion, high yield and high selectivity for producing HFC-245fa.

Another aspect of the present invention is to provide a method as described which does not produce significant amounts of undesirable by-products.

Further aspects and advantages of the present invention will be apparent from the description of the preferred embodiment which follows.

DESCRIPTION OF THE PREFERRED EMBODIMENT

This disclosure of the invention is submitted in furtherance of the constitutional purposes of the U.S. Patent Laws "to promote the progress of science and useful arts" (Article 1, Section 8).

The present invention is based upon the discovery that HFC-245fa may be produced in a process utilizing readily available starting materials such as alkanes and alkenes, particularly carbon tetrachloride ($CCl_4$) and vinyl chloride. The conversions and selectivities for this process are high, rendering the process applicable to commercial scale production. According to one embodiment, a process is provided for preparing halogenated alkanes by reacting a haloalkane and a haloalkene in the presence of a metal chelating agent and iron to produce a halogenated alkane. In a preferred embodiment, the haloakane is $CCl_4$, the haloalkene is vinyl chloride and the metal chelating agent is tributyl phosphate. It was determined that other chelating agents containing phosphorous could be used. It is preferred that the ratio of haloalkane to haloalkene is about 1.07:1. In a preferred embodiment, this reaction occurs at a temperature of about 105° C. and a reaction pressure of 5–15 psig. According to another embodiment of the present invention, the reaction produces 1,1,1,3,3-pentachloropropane. This compound can then be used to form HFC-245fa. One embodiment of the present reaction is demonstrated by the following non-limiting reaction.

EXAMPLE 1

Preparation of 1,1,1,3,3-Pentachloropropane

A 1 inch I.D. by 24 inch long continuous reactor was equipped with a sight glass, circulation pump and pressure control valve. 193 grams of iron wire were added to the reactor followed by the addition of carbon tetrachloride, containing 3% by weight tributyl phosphate. The carbon tetrachloride was added to the reactor in an amount sufficient to fill the reactor to 60% of its total volume. The reactor was then heated to 105° C. and vinyl chloride was fed into the reactor until the 1,1,1,3,3-pentachloropropane concentration in the circulating product stream reached a concentration of 66% by weight. A mixture of 3% tributyl phosphate/carbon tetrachloride and vinyl chloride was then continuously fed into the reactor in a mole ratio of 1.07:1. Reaction pressure was controlled at 5–15 psig and the product was removed by liquid level control. Analysis of the crude product indicated a 75% conversion to 1,1,1,3,3-pentachloropropane.

Another aspect of the present invention provides processes of preparing a halogenated propene by reacting a halopropane in the presence of a Lewis acid catalyst. According to one embodiment of this process, the halopropane is 1,1,1,3,3-pentachloropropane, the Lewis acid catalyst is $FeCl_3$ and the halogenated propene product is 1,1,3,3-tetrachloropropene. Other Lewis acid catalysts are expected to exhibit similar performance. In a preferred embodiment, the reactants are combined at a temperature of 70° C. In another embodiment, the halopropane is produced from a reaction involving a haloalkane and a haloalkene, preferably $CCl_4$ and vinyl chloride. In still another embodiment, this process of the present invention further comprises reacting the halogenated alkene, either in a single or multiple steps to form HFC-245fa.

The temperature of the reaction is generally one which is preferably high enough to provide a desired amount and rate of conversion of the halogenated propene, and preferably low enough to avoid deleterious effects such as the production of decomposition products. The reaction is preferably carried out at a temperature between 30° C. and about 200° C. A more preferred range for the reaction is from about 55° C. to about 100° C. It will be appreciated that the selected temperature for the reaction will depend in part on the contact time employed, in general the desired temperature for the reaction varying inversely with the contact time for the reaction. The contact time will vary depending primarily upon the extent of conversion desired and the temperature of the reaction. The appropriate contact time will in general be inversely related to the temperature of the reaction and directly related to the extent of conversion of halogenated propene.

The reaction can be conducted as a continuous flow of the reactants through a heated reaction vessel in which heating of the reactants may be very rapidly effected. Under these circumstances, the residence time of the reactants within the vessel is desirably between about 0.1 second and 100 hours, preferably between about 1 hour and about 20 hours, more preferably about 10 hours. The reactants may be preheated before combining or may be mixed and heated together as they pass through the vessel. Alternatively, the reaction may be carried out in a batch process with contact time varying accordingly. The reaction can also be carried out in a multistage reactor, wherein gradients in temperature, mole ratio, or gradients in both temperature and mole ratio are employed.

The weight percent of the Lewis acid catalyst employed in this reaction may vary widely and is not critical to the inventive method. Limitations on this ratio are more determined by practical considerations. A preferred range for the weight percent of catalyst is from 0.01% to 40% by weight, based on the weight of halogenated propene and Lewis acid catalyst mixture, preferably about 0.05 to about 1%, with a weight percent of from about 0.05% to about 0.5% by weight, particularly about 0.1% by weight being most preferred. Suitable Lewis acid catalysts include any of the commonly known Lewis acids and include, for example, $BCl_3$, $AlCl_3$, $TiCl_4$, $FeCl_3$, $BF_3$, $SnCl_4$, $ZnCl_2$, $SbCl_5$, and mixtures of any two or more of these Lewis acids.

The reaction can be carried out at atmospheric pressure, or at subatmospheric or superatmospheric pressures. The use of subatomspheric pressures is especially advantageous in reducing the production of undesirable products. By way of non-limiting example, one embodiment of this reaction is demonstrated as follows.

EXAMPLE 2

Dehydrochlorination of 1,1,1,3,3-Pentachloropropane

Into a 500 ml round bottom flask was added 270 grams of 1,1,1,3,3-pentachloropropane. To this was added 2.7 grams anhydrous $FeCl_3$. The slurry was stirred under a pad of nitrogen and heated to 70° C. The solution was sampled at 30-minute intervals to give 1,1,3,3-tetrachloropropene with the following conversions and selectivity:

| Time (min.) | Conversion (area %) | Selectivity (%) |
| --- | --- | --- |
| 30 | 62.52 | 100 |
| 60 | 83.00 | 100 |
| 90 | 90.7 | 99.68 |
| 120 | 94.48 | 99.32 |

In another embodiment of the present invention, reactions of the present invention can be combined to perform a process for the production of HFC-245fa comprising the following steps: (1) reacting carbon tetrachloride with vinyl chloride to produce 1,1,1,3,3-pentachloropropane; (2) dehydrochlorinating the 1,1,1,3,3-pentachloropropane with a Lewis acid catalyst to produce 1,1,3,3-tetrachloropropene; (3) fluorinating the 1,1,3,3-tetrachloropropene to produce HCFC-1233zd; and (4) fluorinating the HCFC-1233zd to produce HFC-245fa. The fluorination reaction of 1,1,3,3-tetrachloropropene with HF, step (3) of the process of the present invention, and the fluorination reaction of HCFC-1233zd with HF, step (4) of the process of the present invention have previously been described. (e.g., U.S. Pat. No. 5,616,819 to Boyce, et al, entitled Process for preparing fluorinated aliphatic compounds).

Other embodiments of the present invention address the difficulty of separating certain halogenated organic compounds and HF, specifically HFC-245fa and HCFC-1233zd. The normal boiling points of HFC-245fa and HCFC-1233zd are 15° C. and 20.8° C., respectively. Normal distillation would separate the HFC-245fa as the lights or overhead product and the HCFC-1233zd as the heavies or bottoms product. However this expected separation does not occur.

Another process of the present invention provides methods for removing HF from a mixture containing HF and a halogenated hydrocarbon by combining the mixture with a solution of inorganic salt and HF and recovering a substantially pure halogenated hydrocarbon. In preferred embodiments of the process the halogenated hydrocarbon is HFC-245fa and the inorganic salt is spray dried KF, the temperature of the solution of inorganic salt and HF is approximately 90° C. and the mole ratio of inorganic salt to HF is about 1:2. Other embodiments of the present invention include the utilization of halogenated hydrocarbons that are crude products of halogenation reactions, such as crude HFC-245fa having impurities of HCFC-1233zd and HF. The present invention also provides an efficient method for regenerating the solution of inorganic salt and HF by removing HF until the mole ratio of inorganic salt to HF is about 1:2. In the preferred embodiment, the HF is removed by flash evaporation.

Without being bound to any theory, it is contemplated that treating a mixture of HF and HFC-245fa with the HF/inorganic salt solution results in absorption of HF by the HF/inorganic salt solution that corresponds to a reduced amount of free HF present with HFC-245fa. Subsequent distillation of the HF/inorganic salt solution treated mixture of HF and HFC-245fa produces essentially pure HFC-245fa, and avoids the separation difficulties associated with mixtures of HF and HFC-245fa. Suitable inorganic salts include alkali metal fluorides such as sodium and potassium fluoride. Suitable molar ratios of alkali metal fluoride to HF range from 1:1 to 1:100, more preferably from 1:2 to 1:4.

The temperature of the HF/inorganic salt solution of this process is preferably between about 50° C. and about 150° C., and more preferably between about 75° C. and about 125° C. The process step can be conducted as a continuous flow of reactants through a heated reaction vessel in which heating of the reactants may be very rapidly effected. The mixture containing the HF and HFC-245fa may be preheated before combining or may be mixed and heated together with the HF/inorganic salt solution as they pass through the vessel. The substantially HF free halogenated hydrocarbon may be recovered as a gas or a liquid.

Following the absorption of HF the resultant HF/inorganic salt solution can be treated to allow recovery of the absorbed HF and regeneration of the original HF/inorganic salt solution. Embodiments of the present invention are demonstrated below by way of non-limiting examples.

EXAMPLE 3

HF Removal From HFC-245fa/HF

To a 600 ml reactor was charged 200 grams of spray-dried KF and 147.47 grams of HF (1:2 mole ratio). The solution was held at 90° C. while 247.47 grams of a 1,1,1,3,3-pentafluoropropane/HF mixture (21.85 wt % HF) was allowed to bubble through the reactor. The analysis of material exiting the reactor indicated that it was approximately 97% (w/w) HFC-245fa; the remainder of the material was primarily HF.

EXAMPLE 4

Regeneration of HF/KF Mixture (HF Recovery)

Following treatment of the HFC-245fa/HF mixture, the HF/KF solution was warmed to 170° C. and HF flashed into a water scrubber until the pressure dropped from 35 psig to 0 psig. Titration of the KF solution showed a KF/HF mole ratio of 1:2.06.

EXAMPLE 5

Isolation of 1,1,1,3,3-Pentafluoropropane

A mixture of HFC-245fa and HF (20.26 wt %) was fed into a reactor with a 2.4 KF/HF (mole ratio) solution at 118° C. After absorbing HF, only 1.94% HF remained in the HFC-245fa. The HF was recovered by vacuum evaporation of the KF/HF solution (molar ratio) as per Example 4, preferably where x≦2, usually 2–3.

In another embodiment, the present invention provides processes for separating HFC-245fa from HCFC-1233zd. In one embodiment, a mixture of HFC-245fa and HCFC-1233zd is distilled to produce a first distillate rich in HCFC-1233zd and a bottom rich in HFC-245fa and the bottom is distilled further to produce a second distillate of essentially HCFC-1233zd free HFC-245fa. In a preferred embodiment, the mixture of HFC-245fa and HCFC-1233zd is the product of a halogenation reaction. In another embodiment, the first distillate is recycled to a halogenation reaction. This process is demonstrated by way of non-limiting example below.

EXAMPLE 6

Azeotropic Distillation of HFC-245fa and HCFC-1233zd

A mixture containing primarily HFC-245fa to be purified by distillation of a lights and a heavies cut is fed to two distillation columns. The first distillation column removes the lights overhead and the bottoms of the first distillation column is fed to a second distillation column. The purified HFC-245fa is removed as the product stream from the overhead of the second distillation column, and the heavies are removed from the bottom of the second distillation column. The concentration of HCFC-1233zd in the overhead stream of the first distillation column was analyzed as 98.36% HFC-245fa with 0.3467% HCFC-1233zd by weight, and this overhead stream can be incinerated or recycled to step (4) of the process (fluorination of 1-chloro-3,3,3-trifluoropropene). The bottoms of the first distillation column was 99.04% HFC-245fa and 43 ppm HCFC-1233zd, and the purified product (HFC-245fa) from the overhead stream of the second distillation column was 99.99% HFC-245fa and 45 ppm HCFC-1233zd.

In another embodiment, the present invention provides processes for separating HFC-245fa from a mixture containing HFC-245fa and HCFC-1233zd. According to one embodiment, the mixture is distilled in the presence of HF to produce a HFC-245fa bottom free of HCFC-1233zd and a distillate. In another embodiment, the distillate is recycled to an HFC-245fa production reaction. The following non-limiting examples are demonstrative of this process.

EXAMPLE 7

Purification of Crude 1,1,1,3,3-Pentafluoropropane

A mixture of crude 1,1,1,3,3-pentafluoropropane containing a small amount of HF was fed into a 1.5" I.D.×120" long distillation column equipped with a condenser and a pressure control valve. The mixture was put into total reflux and then sampled. The results were as follows:

|  | Light | HFC-245fa | HCFC-1233zd | Heavies | HF wt % | Comments |
|---|---|---|---|---|---|---|
| Feed | ND | 99.83 | 0.0898 | 0.0803 | 3.66 |  |
| Top gas vapor | 0.0380 | 98.4143 | 1.4389 | 0.0942 | 3.47 | not near azeotrope |
| Top liquid (reflux) | ND | 99.3024 | 0.6269 | 0.0707 | 19.55 | not near azeotrope |
| Bottom liquid | ND | 99.9405 | ND | 0.0595 | 2.3 |  |

EXAMPLE 8

Purification of Crude 1,1,1,3,3-Pentafluoropropane

A similar test was performed as in Example 7. The results are shown below:

|  | Light | HFC-245fa | HCFC-1233zd | Heavies | HF wt % | Comments |
|---|---|---|---|---|---|---|
| Feed | ND | 99.45 | 0.0758 | 0.4211 | 3.83 | |
| Top gas vapor | ND | 99.78 | 0.191 | 0.01 | 16.95 | not near azeotrope |
| Top liquid (reflux) | ND | 99.81 | 0.164 | 0.025 | 21.21 | not near azeotrope |
| Bottom liquid | ND | 99.64 | 0.007 | 0.393 | 1.95 | |

In accordance with a preferred embodiment of the present invention, HFC-245fa is produced by: (1) reacting carbon tetrachloride ($CCl_4$) with vinyl chloride ($CH_2$=CHCl) to produce 1,1,1,3,3-pentachloropropane ($CCl_3CH_2CHCl_2$); (2) contacting the 1,1,1,3,3-pentachloropropane with a Lewis acid catalyst to produce 1,1,3,3-tetrachloropropene ($CCl_2$=CHCHCl$_2$); (3) fluorination of 1,1,3,3-tetrachloropropene with HF in the liquid phase to produce HCFC-1233zd ($CF_3CH$=CHCl); (4) fluorination of HCFC-1233zd with HF in the liquid phase in the presence of a fluorination catalyst to produce a mixture of HFC-245fa, HF and HCFC-1233zd; (5) treatment of the product mixture from step (4) with an HF/inorganic salt solution to produce a crude product mixture containing HFC-245fa as the major component and minor amounts of HF and HCFC-1233zd; (6) distilling the product mixture from step (5) to produce a bottoms product containing HFC-245fa and a distillate portion containing HF and HCFC-1233zd; and (7) final purification of the bottoms product from step (6) to remove traces of acid, water or other by-products from the HFC-245fa product.

A preferred method of separating the product from by-products, step (6) of the process of the present invention, comprises the separation and recovery of HFC-245fa from the product mixture resulting from step (5), such as by distillation of the mixture to produce bottoms containing the HFC-245fa and a distillate by-product mixture containing HF and olefinic impurities. Batch or continuous distillation processes are suitable for these preparations.

A preferred embodiment of the present invention includes a further purification step (7), wherein the HFC-245fa, isolated as a bottoms product from step (6), is purified via water scrubbing and distillation to remove residual traces of moisture and/or acid. Numerous processes are well known in the art and can be employed for the removal of residual amounts of acid and water, for example treatment with molecular sieves, and the like.

Preferably, step (7) is accomplished by first scrubbing the bottoms product from step (6) and then separating the product by distillation. Scrubbing can be accomplished either by scrubbing the bottoms product with water and then, in a separate step, neutralizing the acid with caustic until the pH is neutral, e.g., 6–8, or by scrubbing in a single step with water and caustic.

What is claimed is:

1. A process for preparing halogenated alkanes whereby a haloalkane and a haloalkene are reacted in the presence of both an alkyl phosphate and iron wire to produce a halogenated alkane.

2. The process of claim 1 wherein the haloalkane comprises carbon tetrachloride, the haloalkene comprises vinyl chloride, and the halogenated alkane comprises 1,1,1,3,3-pentachloropropane.

3. The process of claim 2 wherein the carbon tetrachloride and the vinyl chloride are reacted in a reactor having a temperature of at least 105° C.

4. The process of claim 2 wherein the carbon tetrachloride and the vinyl chloride are reacted in a reactor having a pressure of from about 5 to about 15 psig.

5. The process of claim 2 wherein the alkyl phosphate comprises tributyl phosphate.

6. The process of claim 2 further comprising converting the 1,1,1,3,3-pentachloropropane to 1,1,1,3,3-pentafluoropropane.

7. The process of claim 1 wherein the reacting occurs prior to isolating the halogenated alkane.

8. The process of claim 1 wherein the haloalkane and the haloalkene are reacted in the presence of both the alkyl phosphate and the iron wire within a reactor, the reactor being provided a mixture comprising:
 the haloalkane;
 the haloalkene; and
 the alkyl phosphate.

9. The process of claim 8 wherein the mixture comprises at least two components, the first of the two components consisting of the haloalkane and the haloalkene, the second of the two components consisting of the alkyl phosphate, wherein the mixture comprises about 3% of the second component.

10. The process of claim 9 wherein the first component has a mole ratio of the haloalkane to the haloalkene of about 1.07:1.

11. The process of claim 8 wherein the mixture comprises at least two components, the first of the two components consisting of the haloalkane and the haloalkene, the second of the two components consisting of the alkyl phosphate, wherein the first component has a mole ratio of the haloalkane to the haloalkene of about 1.07:1.

12. The process of claim 1 wherein the haloalkane and the haloalkene are reacted in the presence of both the alkyl phosphate and the iron wire to produce the halogenated alkane within a reactor, further comprising removing at least a portion of the halogenated alkane from within the reactor, wherein the iron wire remains in the reactor during the removing.

13. The process of claim 1 wherein the elongated solid iron mass comprises iron wire.

* * * * *